US007488481B2

(12) United States Patent
Farzan et al.

(10) Patent No.: US 7,488,481 B2
(45) Date of Patent: Feb. 10, 2009

(54) POLYPEPTIDES DERIVED FROM ANTI-HIV-1 GP120 ANTIBODIES THAT ABROGATE GP120 BINDING TO CCR5

(75) Inventors: Michael R. Farzan, Cambridge, MA (US); Tatyana K. Dorfman, Needham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 555 days.

(21) Appl. No.: 10/772,089

(22) Filed: Feb. 5, 2004

(65) Prior Publication Data

US 2004/0192609 A1 Sep. 30, 2004

Related U.S. Application Data

(60) Provisional application No. 60/445,853, filed on Feb. 10, 2003.

(51) Int. Cl.
*A61K 39/21* (2006.01)
*A61K 38/00* (2006.01)

(52) U.S. Cl. .................... 424/188.1; 530/324; 530/325; 530/326

(58) Field of Classification Search ............... 424/188.1
See application file for complete search history.

(56) References Cited

U.S. PATENT DOCUMENTS

2001/0039026 A1   11/2001   Dobbs et al.
2002/0068813 A1    6/2002   Dragic et al.

OTHER PUBLICATIONS

Berger, "HIV Entry and Tropism: The Chemokine Receptor Connection," *AIDS 11*(Supp. A):S3-S16 (1997).
Cole, et al., "Characterization of Neutralization Epitopes of Simian Immunodeficiency Virus (SIV) Recognized by Rhesus Monoclonal Antibodies Derived from Monkeys Infected with an Attenuated SIV Strain," *Virology 290*:59-73 (2001).
Cormier, et al., "Specific Interaction of CCR5 Amino-Terminal Domain Peptides Containing Sulfotyrosines with HIV-1 Envelope Glycoprotein gp120," *Proc. Natl. Acad. Sci. USA 97*:5762-5767 (2000).
Deng, et al., "Identification of a Major Co-Receptor for Primary Isolates of HIV-1," *Nature 381*:661-666 (1996).
Doranz, et al., "Chemokine Receptors as Fusion Cofactors for Human Immunodeficiency Virus Type 1 (HIV-1)," *Immunologic Research 16*:15-28 (1997).
Dragic, et al., "HIV-1 Entry into $CDR^+$ Cells Is Mediated by the Chemokine Receptor CC-CKR-5," *Nature . 381*:667-673 (1996).
Farzan, et al., "A Tyrosine-Rich Region in the N Terminus of CCR5 Is Important for Human Immunodeficiency Virus Type 1 Entry and Mediates an Association between gp120 and CCR5," *J. Virol. 72*:1160-1164 (1998).
Farzan, et al., "Tyrosine Sulfation of the Amino Terminus of CCR5 Facilitates HIV-1 Entry," *Cell 96*:667-676 (1999).
Farzan, et al., "A Tyrosine-Sulfated Peptide Based on the N Terminus of CCR5 Interacts with a CD4-Enhanced Epitope of the HIV-1 gp120 Envelope Glycoprotein and Inhibits HIV-1 Entry," *J. Biol. Chem. 275*:33516-33521 (2000).
Fouts, et al., "Neutralization of the Human Immunodeficiency Virus Type 1 Primary Isolate JR-FL by Human Monoclonal Antibodies Correlates with Antibody Binding to the Oligomeric Form of the Envelope Glycoprotein Complex," *J. Virol. 71*:2779-2785 (1997).
Ho, et al., "Conformational Epitope on gp120 Important in CD4 Binding and Human Immunodeficiency Virus Type 1 Neutralization Identified by a Human Monoclonal Antibody," *J. Virol. 65*:489-493 (1991).
Farzan, M.; *A Tyrosine-sulfated Peptide Based on the N Terminus of CCR5 interacts with a CD4-enhanced Epitope of the HIV-1 gp120 Envelope Glycoprotein and Inhibits HIV-1 Entry.*; Oct. 27, 2000, vol. 275, No. 43, pp. 33516-33521.

*Primary Examiner*—Jeffrey S. Parkin
(74) *Attorney, Agent, or Firm*—Michael A. Sanzo; Law Office of Michael A. Sanzo, LLC

(57) ABSTRACT

The present invention is directed to peptides that are capable of blocking the entry of HIV-1 into host cells by means of the CCR5 receptor. The affinity of the peptides for gp120 on the HIV viral surface may be increased by sulfating tyrosine residues. In addition, the invention is directed to a method for increasing the affinity of antibodies for their antigens by sulfating tyrosine residues in the antibody amino acid chain.

15 Claims, 1 Drawing Sheet

| | | |
|---|---|---|
| 48d | CAA..........................DPWELNAFNVW | (SEQ ID NO:7) |
| 17b | CAG...............VYEGEADEGEYRNNGFLKHW | (SEQ ID NO:8) |
| 47e | CAK...........GGEDGDYLSDPFYYNHGMDVW | (SEQ ID NO:9) |
| 412D | CAS...........PYPNDYNDYAPEEGMSWYFDLW | (SEQ ID NO:10) |
| E51 | CAS....NSIAGVAAAGDYADYDGGYYYDMDVW | (SEQ ID NO:11) |
| C12 | CAR........DVGPDWDNDDYYDRSGRGVFDYW | (SEQ ID NO: 12) |
| SB1 | CAT...........RNPNYDENADYSTVYHYMDVW | (SEQ ID NO:13) |

Figure 1

SEQUENCE LISTING

<160> NUMBER OF SEQ ID NOS: 6

<210> SEQ ID NO 1
<211> LENGTH: 19

<212> TYPE: PRT
<213> ORGANISM: Homo sapiens

<400> SEQUENCE: 1

Gly Gly Glu Asp Gly Asp Tyr Leu Ser Asp Pro Phe Tyr Tyr Asn His
1               5                   10                  15

Gly Met Asp

<210> SEQ ID NO 2
<211> LENGTH: 18
<212> TYPE: PRT
<213> ORGANISM: Homo sapiens

<400> SEQUENCE: 2

Pro Tyr Pro Asn Asp Tyr Asn Asp Tyr Ala Pro Glu Glu Gly Met Ser
1               5                   10                  15

Trp Tyr

<210> SEQ ID NO 3
<211> LENGTH: 15
<212> TYPE: PRT
<213> ORGANISM: Homo sapiens

<400> SEQUENCE: 3

Gly Asp Tyr Ala Asp Tyr Asp Gly Gly Tyr Tyr Tyr Asp Met Asp
1               5                   10                  15

<210> SEQ ID NO 4
<211> LENGTH: 24
<212> TYPE: PRT
<213> ORGANISM: Homo sapiens

<400> SEQUENCE: 4

Asn Ser Ile Ala Gly Val Ala Ala Ala Gly Asp Tyr Ala Asp Tyr Asp
1               5                   10                  15

Gly Gly Tyr Tyr Tyr Asp Met Asp
            20

<210> SEQ ID NO 5
<211> LENGTH: 21
<212> TYPE: PRT
<213> ORGANISM: Homo sapiens

<400> SEQUENCE: 5

Asp Val Gly Pro Asp Trp Asp Asn Asp Asp Tyr Tyr Asp Arg Ser Gly
1               5                   10                  15

Arg Gly Val Phe Asp
            20

<210> SEQ ID NO 6
<211> LENGTH: 19
<212> TYPE: PRT
<213> ORGANISM: Homo sapiens

<400> SEQUENCE: 6

Arg Asn Pro Asn Tyr Asp Glu Asn Ala Asp Tyr Ser Thr Val Tyr His
1               5                   10                  15

Tyr Met Asp

POLYPEPTIDES DERIVED FROM ANTI-HIV-1 GP120 ANTIBODIES THAT ABROGATE GP120 BINDING TO CCR5

CROSS REFERENCE TO RELATED APPLICATION

The present application claims the benefit of U.S. provisional application No. 60/445,853, filed on Feb. 10, 2003, which is incorporated in its entirety herein by reference.

STATEMENT OF GOVERNMENT FUNDING

The invention described herein was made with Government support under NIH Grant No. R01 AI48425 awarded by the Department of Health and Human Services. The Government therefore has certain rights in the invention.

FIELD OF THE INVENTION

The present invention is directed to peptides that can be used to prevent the binding of gp120 to CCR5 receptors on the surface of immune cells. By preventing this interaction, the peptides can be used to block the entry of HIV into cells. In addition, the invention is directed to a method for increasing the affinity of antibodies for antigens by sulfating tyrosine residues in the antibody sequence.

BACKGROUND OF THE INVENTION

The HIV virus responsible for causing AIDS enters immune cells through a multi-step process (Berger, *AIDS* 11:S3-16 (1997); Doranz, et al, *Immunol. Res.* 16:15-28 (1997)). Initially, gp120 located on the HIV viral surface binds to a CD4 receptor on the surface of the host cell. This causes the gp120 protein to undergo a conformational change that allows it to bind to a second cell surface receptor, CCR5 (Dragic, et al., *Nature* 381:667-673 (1996); Deng, et al., *Nature* 381:661-666 (1996)). It is this second binding step that ultimately leads to membrane fusion and viral entry.

Biochemical studies have revealed that a portion of the CCR5 receptor near its amino terminus is critical for interaction with gp120 and that there are several sulfated tyrosines in this region that are essential for binding (Farzan, et al, *J. Virol.* 72:1160-1164 (1998); Farzan, et al., *Cell* 96:667-676 (1999)). Attempts have been made to model peptides based upon the CCR5 binding region and use them to block the entry of HIV into immune cells (Farzan, et al., *J. Biol. Chem.* 275:33516-33521 (2000); Cormier, et al., *Proc. Nat'l Acad. Sci.* 97:5762-5767 (2000)). However, the peptides that have been developed thus far appear to have relatively low affinity for gp120 and this may ultimately limit their clinical usefulness.

In an alternative approach, researchers have attempted to make antibodies against gp120 that block the entry of HIV into host cells (see, e.g., Cole, et al., *Virology* 290:59-73 (2001); Fouts, et al., *J. Virol.* 71:2779-2785(1997); Ho, et al., *J. Virol.* 65:489-493 (1991)). Although antibodies of this type have a high affinity for antigen, developing them for use as a long term therapy may be difficult and the cost of production is likely to be quite expensive.

SUMMARY OF THE INVENTION

The present invention is based upon experiments in which antibodies blocking HIV cellular entry were structurally analyzed. Surprisingly, it was found that the region of the antibody binding to gp120 has sulfated tyrosines, a characteristic also present in CCR5. This led to the concept that it is possible to increase the affinity of antibodies for antigens by sulfating tyrosines in the antibody amino acid sequence. One preferred method of doing this is to produce the antibodies in vivo under conditions which allow sulfation to take place to the same extent as would occur in nature. In addition, the structural information provided by the analysis of antibodies has allowed peptides to be designed and synthesized which mimic the antibody's ability to block the cellular entry of HIV. These peptides may be used by researchers studying AIDS and by clinicians attempting to develop new approaches to controlling HIV infection.

In its first aspect, the invention is directed to a peptide that is no more than 20-30 amino acids in length and which includes at least 15 contiguous amino acids selected from any one of the following sequences:

(a) GGEDGDYLSDPFYYNHGMD (SEQ ID NO:1), in which the tyrosine at position 7 must be present in any sequence selected;

(b) PYPNDYNDYAPEEGMSWY (SEQ ID NO:2), in which the tyrosines at positions 2 and 6 must be present in any sequence selected;

(c) GDYADYDGGYYYDMD (SEQ ID NO:3), in which at least one of the tyrosines at positions 3, 10, 11 or 12 must be present in any sequence selected;

(d) NSIAGVAAAGDYADYDGGYYYDMD (SEQ ID NO:4), in which at least one of the tyrosines at positions 12, 19, 20 or 21 must be present in any sequence selected;

(e) DVGPDWDNDDYYDRSGRGVFD (SEQ ID NO:5), in which the tyrosine at position 11 must be present in any sequence selected; and (f) RNPNYDENADYSTVYHYMD (SEQ ID NO:6), in which the tyrosine at position 5 must be present in any sequence selected.

All of the sequences shown above begin at the N terminus (on the left) and end with the C terminus (on the right). The sequences are based upon corresponding sequences present in the portion of antibodies recognizing and binding to gp120 (see FIG. 1). Peptides should only contain the l-amino acids that are commonly recognized in the art as being present in mammalian proteins and, in each case, it is preferred that at least one of the tyrosines in the chosen peptide be sulfated. It is particularly preferred that sulfation occur at the tyrosines that are noted above as being required in selected sequences, For example, the tyrosine at position 7 in SEQ ID NO:1 should be sulfated.

It will be recognized by those of skill in the art that conservative amino acid substitutions, e.g., substituting one acidic or basic amino acid for another, can often be made without affecting the biological activity of a peptide or protein. Minor variations in sequence of this nature may be made in any of the peptides shown, provided that these changes do not substantially (e.g., by 15% or more) reduce the ability of the peptide to neutralize the entry of HIV-1 into immune cells. Neutralization may be tested using the method described in the Examples section, although other similar assays that have been described in the art for measuring the entry of virus into cells may also be employed. In all cases, a sulfated tyrosine may be replaced with tyrosine sulfonate or phenylalanine methyl sulfatate.

The peptides described above may be either used alone or in conjunction with other agents that are useful in the treatment or study of the HIV-1 virus. For example, the peptides can be used with agents that reduce the entry of HIV into cells by inhibiting the interaction between the virus and the CD4 receptor. In one preferred embodiment one or more of the peptides is made in the form of a fusion protein in which it is joined to: the CD4 receptor; a virus-binding peptide derived from the CD4 receptor; or an antibody blocking CD4/virus binding. Such fusion proteins would block viral entry into cells at two different levels and should therefore be especially effective.

The invention also includes polynucleotides coding for the peptides described above. In particular, the polynucleotide should include a sequence coding for at least 15 contiguous amino acids selected from the sequences shown as SEQ ID NO:1-SEQ ID NO:6. These polynucleotides may be incorporated into an expression vector in which it is operably linked to a promoter. The term "operably linked " means that the promoter and coding sequence are joined in a manner that allows them to carry out their normal functions, i. e., transcription of the coding sequence is under the control of the promoter and the transcript produced is correctly translated into the desired peptide. The expression vector may be used to transform a host cell which can then produce the peptide. Once made, the peptide can either be isolated or its effects on biological functions can be studied directly.

In addition, the invention is directed to peptides consisting essentially of the amino acid sequence of SEQ ID NO:1, SEQ ID NO:2, SEQ ID NO:3, SEQ ID NO:4, SEQ ID NO:5, or SEQ ID NO:6. The term "consisting essentially of" includes peptides having exactly the sequences shown herein as well as peptides with differences that are not substantial as evidenced by their retaining the basic and novel characteristics of the shown peptides. For the purposes of the present invention, the basic and novel characteristic of each peptide is defined as its ability to prevent the entry of HIV-1 into cells by means of the CCR5 receptor. Any peptide having a structural change that reduces this ability is not part of the invention.

The term "consisting essentially of" also requires that the amino acid sequence of any peptide encompassed by the invention must be at least 80% homologous with the sequences shown herein with a homology of 90% or better being preferred. There is also a requirement that certain tyrosines be present in sequences. Specifically, the tyrosine at position 7 must be present in any peptide based upon SEQ ID NO:1; the tyrosines at positions 2 and 6 must be present in any peptide based upon SEQ ID NO:2; at least one of the tyrosines at positions 3, 10, 11 or 12 must be present in any peptide based upon SEQ ID NO:3; at least one of the tyrosines at positions 12, 19, 20 or 21 must be present in any peptide based upon SEQ ID NO:4; the tyrosine at position 11 must be present in any peptide based upon SEQ ID NO:5; and the tyrosine at position 5 must be present in any peptide based upon SEQ ID NO:6. It is also preferred that some or all of these particular tyrosines be sulfated and other tyrosine residues present in peptides may, optionally, also be sulfated. As discussed above, the sulfated tyrosines may be replaced with either tyrosine sulfonate or phenylalanine methyl sulfatate. The invention includes polynucleotides coding for the peptides, expression vectors in which these peptides are operably linked to a promoter, and host cells transformed with the expression vectors.

Functionally, the peptides described above should reduce the uptake of an R5 HIV isolate by cultured CCR5-positive immune cells by at least 50% at a concentration of 1 microgram per ml. The peptides may be used in a method of preventing the binding of gp120 to CCR5 by carrying out incubations between ligand and receptor in the presence of an effective concentration of peptide. This method may serve as an assay for determining whether a particular HIV strain enters cells through the CCR5 receptor or by some alternative means. Such assays are of interest not only in medical research, but also as a diagnostic tool for determining the type of virus that has infected a patient and the likelihood that such a patient would respond to a therapy based upon blocking the binding of gp120 to CCR5. The peptides can also be used as therapeutic agents in the treatment of HIV infected patients.

In another aspect, the invention is directed to a method of modifying antibodies by sulfating tyrosine amino acids in their primary structure. This may be accomplished either chemically or by producing the antibodies in vivo in cells where tyrosine sulfotransferases are either naturally present or in cells which have been engineered to make such enzymes. The antibodies may then be tested and compared with their unmodified counterparts to determine whether their affinity for antigen has been increased. This method is likely to be particularly successful in cases where the antigen is a ligand such as gp120 that binds to a region of a receptor or other molecule in which tyrosine sulfates are present. As with the peptides described above, sulfated tyrosines in antibodies may be replaced with either tyrosine sulfonate or phenylalanine methyl sulfatate.

BRIEF DESCRIPTION OF THE DRAWING

FIG. 1: FIG. 1 shows the CDR3 region and adjacent residues of antibodies characterized in the studies described in the Examples section below.

DETAILED DESCRIPTION OF THE INVENTION

The present invention is based upon structural studies performed on antibodies that bind to gp120 and prevent it from interacting with CCR5. These studies revealed that the sequences shown in FIG. 1 are directly responsible for antibody binding and, surprisingly, it was discovered that tyrosines in these sequences are sulfated. Peptides based upon the sequences shown in FIG. 1 may also be used to prevent the interaction between gp120 and CCR5. The peptide sequences are the same except that they do not have the first three residues (CAS, for example) or the last two (LW, for example). Exact peptide sequences that may be used are shown herein as SEQ ID NO:1-SEQ ID NO:6.

Additional studies have suggested that certain tyrosine residues are very important for full activity. For example, for peptides based upon E51, i.e., peptides designated as SEQ ID NO:3 and SEQ ID NO:4, it appears that the three consecutive tyrosines near the C terminus, i.e., residues 10-12 in SEQ ID NO:3 and residues 19-21 in SEQ ID NO:4, must be present for full activity. In the case of E51 peptides, it was found that the shorter sequence shown as SEQ ID NO:3 is just as effective as the longer sequence, SEQ ID NO:4. Other studies revealed that the first tyrosine of peptides based upon 47e must be sulfated and the first two tyrosines of peptides based on 412d must be sulfated to maintain full activity.

Peptides may be made by any of the means that are well known in the art, with chemical synthesis being generally preferred. Sulfation can be accomplished in at least three different ways. First, peptides can be synthesized using standard procedures except that tyrosine sulfate is used in the place of tyrosine. Alternatively, sulfation can be accomplished in vivo using cells, which have been transfected with plasmids encoding an appropriate enzyme, e.g., tyrosine protein sulfotransferase 2. Under these conditions, sulfation is quite specific to particular residues and should not occur art sites at which sulfation would not normally be present. Finally, synthesized peptide may be exposed to a tyrosine sulfotransferase and PAPS (a small molecule donor of sulfate) in a cell-free system. However, sulfation is usually less efficient using this procedure than when carried out in vivo.

Once produced, peptides may be purified using procedures that are well known in the art. For example, they may be purified directly from resins used in solid state synthetic methods using antibodies directed against the peptides or by producing peptides in a form in which they are fused to a moiety that aids in purification and which can then be cleaved. Any of the methods that have been described in the art for purification are compatible with the present invention.

Assays for determining the ability of peptides to interfere with the binding of gp120 to CCR5 may be carried out using procedures well known in the art and are evidenced by the inhibition of viral entry into cultured immune cells. These assays may be carried out using luciferase-expressing HIV-1 as described in the Examples section below. The amount of virus entering cells in the absence of peptide and in the presence of peptide can be compared over a range of peptide concentrations to determine an $EC_{50}$.

Inhibitory peptides may also be administered to patients as a treatment for HIV-1 infection. In order to avoid destruction of peptides in the gastrointestinal tract, they should typically be administered parenterally, preferably by injection. Dosages may be determined using methods well known in the area of clinical medicine and should be sufficient to substantially reduce the amount of HIV infecting immune cells. The compositions administered may be prepared as part of a pharmaceutical composition using methods of formulation that are well established (see, e.g., *Remington's Pharmaceutical Sciences*, $16^{th}$ ed., A. Oslo ed., Easton, Pa. (1980)).

In addition, the peptides may be combined with other therapeutic agents used for treating HIV-1 to increase overall effectiveness. Combination may take the form of timing the administration of the separate drugs so that their therapeutic effects overlap or the drugs may be given together in a single pharmaceutical composition. The peptides may also be fused to another therapeutic agent. For example, in the case where the other agent is a protein (e.g., a protein that acts at an HIV receptor), a fusion construct can be made that includes both this protein and one or more of the inhibitory peptides described herein.

Apart from peptides, the invention also includes antibodies in which tyrosine residues are modified by sulfation as a means for increasing the affinity of the antibody for antigen. Sulfation may be carried out using any of the methods discussed herein with respect to the sulfation of peptides. Once modification of the antibody residues is complete, a comparison can be made between sulfated antibodies and their non-sulfated counterparts. In particular, binding assays may be performed in order to determine whether the modification of the tyrosine residues has altered the affinity of the antibody for antigen. It is expected that an increase in affinity is likely to occur in cases where the antigen normally binds to a receptor or other molecule by means of sulfate bonds. A good example of the increased affinity that can be obtained by this procedure is described herein with respect to antibodies directed at gp120.

EXAMPLES

A. INTRODUCTION

The complementarity determining region 3 (CDR3) of the antibody heavy chain is the most diverse, and usually the most functionally important, antigen binding domain. Unlike the CDR1 and CDR2 domains, which derive directly from the variable region genes, the heavy chain CDR3 derives primarily from one of 23 functional diversity (D) region genes together with one of six joining (J) region genes. The junctions bounding the D-region are also modified by N- and P-linked addition. Most D-region genes encode sequences disproportionately rich in tyrosines. Some of these sequences—for example diversity genes 3-9, 3-22, 4-11, 4-17, and 5-12—are very similar to regions of proteins known to be tyrosine sulfated, and nine of 23 D genes encode sequences of one or more tyrosines immediately adjacent to an aspartic acid, a motif present at most sites of tyrosine sulfation. This apparent bias in D-gene-encoding sequences, combined with the well-documented ability of tyrosine sulfation to enhance the affinity of receptor-ligand associations, suggests that this modification may play an integral role in the human humoral response, especially, as is the case with HIV-1, when the target antigen itself binds sulfated tyrosines.

In the present Example, we demonstrate that human antibodies can be modified in their heavy chain CDR3 regions by functionally important sulfate groups that contribute to their ability to bind antigen. We identify several such antibodies, derived from two HIV-1-infected individuals chosen for their potently neutralizing anti-sera. These antibodies bind gp120 more efficiently in the presence of CD4, and specifically compete for gp120 with sulfated peptides based on the CCR5 amino-terminus. They further emulate CCR5 by associating with the gp120 proteins of R5- but not X4-isolates, and, in contrast to previously described CD4-inducible antibodies, efficiently neutralize these isolates. Thus, what may be a fairly common antibody modification can enhance the humoral response to HIV-1 and perhaps other pathogens.

B. Methods

Tyrosine Sulfation of Antibodies Against the HIV-1 Envelope Glycoprotein

Transformed human B-cells from HIV-1 infected individuals were radiolabeled with [$^{35}$S]-cysteine and -methionine, or [$^{35}$S]-sulfate alone. Supernatants were harvested, precipitated with Protein A-Sepharose, and analyzed by SDS-PAGE to separate heavy and light antibody chains. Single-chain antibody constructs (scFv) prepared from transformed B-cell lines (17b, E51) or selected from a phage display library generated from an HIV-1 infected individual with a potent neutralizing titer (C12, SB1) were radiolabeled as described above, precipitated with Protein L, and analyzed by SDS-PAGE.

Incorporation of Sulfate into Antibody Chains

Plasmids encoding various single-chain antibody constructs (scFv) were generated and transfected into 293T cells. Cells were then divided, and labeled with [$^{35}$S]-cysteine and -methionine, or [$^{35}$S]-sulfate alone. Supernatants of radiolabeled cells were immunoprecipitated with Protein L-Sepharose, and analyzed for sulfate incorporation. Supernatants from [35S]-cysteine and -methionine labeled cells were also incubated with the gp120 molecules of various HIV-1 isolates and CD4-Ig, and immunoprecipitated with Protein A-Sepharose to determine association of the scFv with CD4-bound gp120.

Contribution of Sulfated Tyrosines to Antibody Affinity

An scFv of the sulfated antibody 47e was modified by altering the first tyrosine of its CDR3 to phenylalanine. Plasmids encoding wild-type 47e scFv (wt) and this variant ('Y/F') were transfected into 293T cells, which were subsequently radiolabeled with [$^{35}$S]-cysteine and -methionine, or [$^{35}$S]-sulfate. Supernatants of transfected cells were immunoprecipitated with Protein L-Sepharose and analyzed by SDS-PAGE. Radiolabeled 47e scFv (wt) and its Y/F variant were incubated with CD4-Ig and the gp120 of the primary HIV-1 isolates ADA and YU2. Incubated proteins were immunoprecipitated with Protein A-Sepharose and analyzed by SDS-PAGE.

This experiment was repeated except that a single-chain molecule derived from the antibody 412d (wt) and a variant of this scFv in which the first two tyrosines of the 412d CDR3 were altered to phenylalanines ('FF') were analyzed.

The same experiment as repeated again except that the 412d scFv and its FF variant were analyzed for association with CD4-Ig and the gp120 molecules of the HIV-1 isolates ADA, YU2, and JR-FL.

Correlation Between Sulfation Efficiency and Affinity of Sulfated Antibodies for HIV-1 gp120

A plasmid encoding the E51 scFv was cotransfected into 293T cells with a plasmid expressing shRNA complementary to message of the two known tyrosyl protein sulfotransferases (ST-shRNA), unmodified pcDNA3.1 (vector), or plasmid encoding tyrosine protein sulfotransferase 2 (TPST2). Transfected cells were divided and radiolabeled with [$^{35}$S]-cysteine and methionine, or [$^{35}$S]-sulfate, immunoprecipitated with Protein L-Sepharose and analyzed by SDS-PAGE. Radiolabeled supernatants from [$^{35}$S]-cysteine and -methionine labeled cells were incubated with CD4-Ig and the gp120 molecule of the HIV-1 isolate ADA, immunoprecipitated with Protein A-Sepharose, and analyzed by SDS-PAGE.

Examination of Whether Tyrosine-Sulfated Antibodies Mimic CCR5

Radiolabeled single-chain antibody constructs (scFv) were incubated with radiolabeled gp120 of the ADA isolate in the presence and absence of soluble CD4. Protein mixtures were immunoprecipitated with Protein L-Sepharose and analyzed by SDS-PAGE. Ratios of gp120 precipitated in the presence and absence of soluble CD4 were calculated by densitometry. Radiolabeled scFv was incubated with ADA gp120 and CD4-Ig in the presence of peptide buffer (buffer only), an unsulfated peptide derived from the first 22 residues of the CCR5 amino-terminus (c22), a peptide derived from the first 22 residues of the CCR5 amino-terminus in which tyrosines 10 and 14 are sulfated (s22), or a peptide derived from residues 7-28 of the C5a receptor sulfated at the tyrosines corresponding to residues 11 and 14 of the C5a receptor (c5aR-s22). Protein and peptide mixtures were immunoprecipitated with Protein A-Sepharose and analyzed by SDS-PAGE.

Association of Sulfated Antibodies With gp120 of Isolates that Use CCR5

Radiolabeled gp120 molecules of HIV-1 isolates were incubated with CD4-Ig and radiolabeled scFv of antibody molecules. Protein mixtures were then immunoprecipitated with Protein A-Sepharose and analyzed by SDS-PAGE. ADA, YU2, and JR-FL isolates utilize CCR5 but not CXCR4, whereas HXBc2 utilizes CXCR4 exclusively.

Radiolabeled gp120 molecules of HIV-1 isolates were incubated with CD4-Ig and radiolabeled scFv of the 412d antibody. Protein mixtures were analyzed as in described above.

Neutralization of Primary HIV-1 Isolates by Sulfated Antibodies

Luciferase-expressing HIV-1 pseudotyped with the envelope glycoprotein of the R5-isolate ADA or the X4-isolate HMBc2 were incubated with the antibody 412d or 48d and CF2Th cells stably expressing CD4 and CCR5 (ADA infection) or CXCR4 (HXBc2 infection). Cells were washed after one hour and luciferase activity was measured. Other experiments were similar except that virus pseudotyped with the envelope glycoproteins of the R5-isolate ADA, the R5X4-isolate 89.6, the X4-isolate HXBc2, or of the amphotrophic murine leukemia virus (A-MLV) were assayed in the presence of the antibody 17b, the CD4 binding site antibody F105, 412d, or E51.

Effect of Peptide Constructs on Viral Entry into Host Cells

HIV-1 virus expressing green fluorescent protein (GFP) and pseudotyped with the envelope glycoprotein of the 89.6 isolate was incubated (20,000 cpm reverse transcriptase activity per ml) with PM1 cells (a T cell line that naturally expresses HIV-1 receptors and coreceptors), in the presence of varying amounts of pE51-Ig (sulfated peptide fused to the Fc region of human IgG1), R5T3-Ig (a sulfated peptide based on CCR5), or an irrelevant control Ig construct. Cells were washed after one hour, and infection, as indicated by FACS analysis of GFP fluorescence, was measured after 96 hours.

C. Results

Sulfation of Human Antibodies

We initially investigated a set of antibodies obtained from an HIV-1 infected individual, subject AC-01, selected for his ability to control viremia following structured interruption of antiretroviral therapy, and for the potent ELISA response of his serum to the HIV-1 envelope glycoprotein. Amino-acid sequences obtained of the CDR3 regions of the heavy chains of these antibodies suggested the possibility that the tyrosines of some of these antibodies were modified by sulfate (FIG. 1). Virally transformed B-cells expressing these antibodies, or expressing the previously characterized antibodies 17b and 48d, were metabolically labeled with [$^{35}$S]-cysteine and -methionine and in parallel with [$^{35}$S]-sulfate. Cell supernatants were harvested, immunoprecipitated with Protein A-Sepharose, and analyzed by SDS-PAGE. For all antibodies tested, heavy and light chains were visible in lanes from cells labeled with [$^{35}$S]-cysteine and -methionine, whereas only the heavy chain of the antibodies 47e, 412d, CM51, and E51 were labeled with [$^{35}$S]-sulfate. No sulfate was incorporated into the antibodies 17b and 48d. The antibodies derived from subject AC-01 were generated from distinct J and light chains, although, interestingly, each derived from the V1-69 heavy variable chain, as did 17b obtained from a different patient. We conclude that subject AC-01 expresses a number of independent antibodies whose heavy chains are modified by sulfate.

We also investigated single-chain antibody molecules originally selected by phage display from a library generated from another HIV-1 infected individual, FDA-2, selected for his unusually potent neutralizing serum. Plasmids encoding two of these single-chain molecules, along with those expressing single-chain molecules of the antibodies 17b and E51, were transfected into 293T cells. Transfected cells were labeled with either [$^{35}$S]-cysteine and -methionine or [$^{35}$S]-sulfate, and cell supernatants were immunoprecipitated with Protein L-Sepharose and analyzed by SDS-PAGE.

The single-chain antibody molecules C12 and SB 1 were found to efficiently incorporate [$^{35}$S]-sulfate, as did a single-chain molecule generated from E51. In contrast, a single-chain antibody derived from 17b did not incorporate [$^{35}$S]-sulfate. Again, SB1 and C12 are formed from distinct J and light chains, although, strikingly, both obtained from the V1-69 heavy chain. Thus, sulfate-modified antibodies can be readily obtained from at least two individuals with potently neutralizing titers.

Tyrosine Sulfate Contributes to Antibody Affinity

We next investigated the location and function of the sulfate moieties present on antibodies. A single-chain molecule derived from the sulfated antibody 47e (47e scFv), and a variant of this scFv in which the first tyrosine of its heavy chain CDR3 was altered to phenylalanine (Y/F), were characterized. Only 47e scFv, and not the Y/F variant, could incorporate [$^{35}$S]-sulfate. We conclude that the antibody 47e is sulfated exclusively at a single tyrosine of its heavy chain CDR3.

Our results also indicated that the sulfate group present on the 47e single-chain molecule makes a critical contribution to its association with the gp120 molecules of one of two primary isolates assayed. [$^{35}$S]-cysteine and -methionine labeled 47e scFv and its Y/F variant were incubated with metabolically labeled HIV-1 gp120 of the isolates ADA and YU2, together with unlabeled CD4-Ig. Protein mixtures were immunoprecipitated with Protein A-Sepharose and analyzed by SDS-PAGE. It was found that 47e scFv binds, and is efficiently precipitated by, ADA gp120, whereas only very inefficient association of the Y/F variant with ADA gp120 was observed. However, both scFv molecules could be efficiently precipitated by the gp120 molecule of the YU2 isolate bound to CD4-Ig. We conclude that the sulfate present on the antibody 47e contributes substantially to the ability of this antibody to bind the envelope glycoprotein of the ADA, but not the YU2, isolate. We have previously observed that entry of the YU2 isolate is less dependent than that of the ADA isolate on the presence of sulfate at the CCR5 amino-terminus.

Using this same approach, we investigated the role of sulfate moieties present on the 412d antibody. We found that a single-chain molecule of 412d (412d scFv) efficiently incorporates [$^{35}$S]-sulfate, whereas a variant of 412d scFv (denoted as FF), in which the first two tyrosines of its heavy chain CDR3 were altered to phenylalanines, did not. It was also found that 412d scFv can be efficiently immunoprecipitated with CD4-Ig bound to the gp120 molecule of each of three primary HIV-1 isolates. In contrast, substantially less FF scFv could be precipitated by these gp120 molecules bound to CD4-Ig. ADA gp120 again exhibited the greatest dependence on the sulfate groups of 412d, as it did with 47e. We conclude that 412d is sulfated exclusively on tyrosines of its heavy chain CDR3, and that these sulfate groups contribute to the binding of this antibody to envelope glycoprotein of at least three primary HIV-1 isolates. Additional data suggested that sulfate present on the antibodies E51, SB 1, and C12 are also localized exclusively to their heavy chain CDR3 regions. All the remaining tyrosines present on these antibodies, and their adjacent residues, are homologous with those on 47e, 412d, or the unsulfated antibody 17b.

We examined the finctional role of tyrosine sulfation of the E51 antibody by altering the efficiency of the sulfotransferase activity in E51 scFv-expressing cells. A plasmid encoding the E51 single-chain molecule was cotransfected into 293T cells with plasmids encoding shRNA (denoted ST-shRNA) capable of interfering with the message of each of the known tyrosyl protein sulfotransferases (TPST1 and TPST2). E51 scFv-expressing plasmid was also cotransfected with empty vector, or with a plasmid expressing TPST2. Cells were then divided and radiolabeled with [$^{35}$S]-cysteine and -methionine or [$^{35}$S]-sulfate. Cell supernatants were harvested and immunoprecipitated with Protein L-Sepharose. Analysis by SDS PAGE indicated that E51 scFv produced in cells expressing shRNA targeting TPST1 and TPST2 was much less efficiently sulfated than that produced in cells without shRNA. Also, E51 scFv from cells expressing exogenous TPST2 was substantially more sulfated than that from cells lacking exogenous tyrosyl protein sulfotransferase. Other experiments indicated that E51 scFv associates with ADA gp120 in direct proportion to the efficiency with which it is sulfated. Neither shRNA against the sulfotransferases nor exogenous TPST2 had any effect on the sulfate incorporation or gp120 association of the 17b scFv. We conclude that sulfated tyrosines at the heavy chain CDR3 of the E51 antibody contribute to its ability to associate with the gp120 molecule of the ADA isolate.

Sulfated Antibodies Emulate CCR5

17b and 48d are well-characterized examples of antibodies whose binding to gp120 is enhanced by CD4. The sulfated antibodies 47e, 421d, E51, SB1, and C12 were also found to belong to this class. Single-chain molecules of these antibodies and of 17b were immunoprecipitated with Protein L-Sepharose in the presence and absence of soluble CD4. In each case except that of E51 scFv, binding of the single-chain antibody to gp120 was enhanced at least two-fold by soluble CD4. In the case of E51 scFv, binding to gp120 was increased by approximately 40% in the presence of CD4.

Each of the single-chain molecules was incubated with ADA gp120 and CD4-Ig. Peptides previously characterized for their ability to block the association of gp120 with CCR5 were added to each mixture of scFv, ADA gp120, and CD4-Ig. An unsulfated peptide derived from the 22 amino-terminal residues of CCR5 (c22) was found to have no significant effect on the ability of any of the scFv to bind ADA gp120. However, the same peptide with sulfate groups at tyrosines 10 and 14 inhibited the association of each of the scFv to the sulfated antibodies with ADA gp120. A very modest inhibition of association of these scFv molecules was also observed in the presence of a doubly sulfated peptide based on the amino-terminus of the C5a receptor. This latter peptide did not have a noticeable effect on the association of gp120 with CCR5. These data imply that the sulfated antibodies 47e, 412d, E51, SB1, and C12 bind a CD4-enhanced epitope of HIV-1 that includes the binding domain of the CCR5 amino-terminus.

We further investigated the degree to which these sulfated antibodies replicate properties of the CCR5 coreceptor. E51, C12, 412d, SB1, and 17b single-chain molecules were incubated with CD4-Ig and gp120 molecules of the primary R5-isolates ADA, YU2, or JR-FL, or of the laboratory-adapted X4-isolate HXBc2, immunoprecipitated with Protein A-Sepharose, and analyzed by SDS-PAGE. Each of these single-chain antibodies efficiently bound the gp120 of all the R5-isolates, but only the 17b and, unexpectedly, the E51 scFv bound the gp120 of the X4-isolate HxBc2.

We further characterized the range of envelope glycoproteins recognized by the 412d scFv. It was found that 412d scFv associated with the gp120 of all R5-isolates examined, including the clade C isolate SA32 and three clade B isolates. It also associated with the clade B R5X4-isolate 89.6, but not the clade C R5X4-isolate MCGP1. No association was observed with the gp120 molecules of any X4-isolates, including clade B isolates HXBc2 and MN, the clade C isolate SG3, and the clade D isolate ELI. Thus, the 412d antibody preferentially associates with a range of R5-isolates, but not with closely related X4-isolates.

Neutralization of Primary HIV-1 Isolates

We compared the antibodies E51 and 412d with 17b, 48d, and a well-characterized CD4-binding site antibody, F105, for their ability to neutralize HIV-1 pseudotyped with various envelope glycoproteins. It was found that the antibody 48d can neutralize the laboratory-adapted virus HXBc2, but was substantially less efficient at neutralizing the primary R5-virus ADA. In contrast, 412d could efficiently neutralize the ADA virus, but could not neutralize the HXBc2 virus. A potent neutralization of primary isolates was observed with the E51 antibody.

Both 412d and E51 neutralized the ADA virus more efficiently than did 17b. 412d neutralized ADA virus comparably to F105, with $EC_{50}$s between 0.2 and 0.5 μg/ml, whereas the $EC_{50}$ of E51 was substantially less than 0.05 μg/ml. The $EC_{50}$ observed for 17b was greater than 2 μg/ml. E51 and 412d were more efficient than 17b and F105 at neutralizing the primary R5X4-isolate 89.6. In contrast, F105 was most efficient at neutralizing the X4-isolate HXBc2, with 17b and E51 exhibiting lower neutralization efficiency. Again, 412d did not neutralize HXBc2.

None of the antibodies tested neutralized HIV-1 pseudotyped with the envelope glycoprotein of the amphotrophic murine leukemia virus (A-MLV). These data demonstrate that these tyrosine-sulfated antibodies neutralize primary R5- and R5X4-isolates more efficiently than previously characterized CD4-inducible antibodies, but are substantially less capable of neutralizing an X4-isolate.

Inhibition of Entry of Virus into Host Cells

Using a common tissue culture assay system of viral entry, it was found that the peptide-Ig construct (E51-Ig) blocked HIV-1 entry with an $EC_{50}$ of 70 nM. In contrast R5T3-Ig was found to have an $EC_{50}$ of about 50 micromolar (almost 1000× worse than pE51-Ig).

D. Discussion

HIV-1 neutralizing antibodies contribute to the control of viremia and can be used to block transmission of virus to uninfected rhesus macaques. Here we describe a subset of anti-gp120 antibodies that appear to have properties distinct from any thus far characterized. This subset belongs to the class of CD4-inducible antibodies for which 17b and 48d serve as prototypes. Like 17b and 48d, the antibodies described here bind a gp120 epitope that is further exposed by CD4. Unlike 17b and 48d, these antibodies appear to preferentially associate with, and efficiently neutralize, primary R5-isolates, and, most interestingly, are modified in their heavy chain CDR3 by tyrosine sulfation, the same modification present on CCR5. As in the case of CCR5, these sulfate moieties appear to directly contribute to association of these antibodies with gp120. Moreover, the epitope of these antibodies significantly overlaps the region of gp120 that binds the sulfated CCR5 amino-terminus. These and similar antibodies may therefore serve as better soluble surrogates for CCR5 in structural and biochemical studies of the HIV-1 envelope glycoprotein than any protein described to date.

It is also possible that properties of this subset of antibodies are useful in controlling HIV-1. As noted, sulfated antibodies were obtained from two individuals with potent anti-gp120 activity in their sera. In particular, subject A101, the source of E51, 412d, and 47e, exhibited a persistently strong autologous neutralizing response during and following two interruptions of highly active anti-retroviral therapy, HAART. This patient was also exceptional in that sera obtained at the outset of the study continued to efficiently neutralize virus from the same patient well over a year later, indicating either the absence of viral evolution, or the presence of antibodies targeting a conserved region of gp120. The efficiency of HIV-1 neutralization by 412d and especially E51, and their association with the CCR5-binding domain of gp120, are consistent with the latter possibility. Tyrosine-sulfated anti-gp120 antibodies may therefore in some instances correlate with longer-term antibody control of viremia. Our data also show that sulfated CD4-inducible antibodies can be significantly more potent in neutralizing primary virus than the prototypical CD4-inducible antibodies 17b and 48d. Given the conservation of much of the gp120 CCR5-binding domain, these observations suggest that more emphasis should be placed on eliciting antibodies that bind this epitope.

This study also casts some light on the characteristics of antibodies that bind the CCR5 binding domain, and on heavy chain genes that contribute to the likelihood of sulfation. One striking observation is that all the sulfated antibodies, and also 17b, obtained from a total of three individuals, originate from a common variable chain, V1-69. This apparent tendency toward the use of V1-69 could arise from the ability of the heavy chain CDR1 and 2 regions of this variable chain to bind gp120 and orient the antibody so as to place its CDR3 at or near the CCR5-binding region. It is unlikely, however, that V1-69 predisposes an antibody toward sulfation, as both sulfated and unsulfated CD4-inducible antibodies derive from this gene. However, the heavy chain CDR3 of three of five sulfated antibodies (47e, E51, and SB1) derive from J6, one of six heavy chain joining genes. This use of J6 likely reflects the fact that it encodes five sequential tyrosines at its 5' end, and also that it is the longest of the J chain genes, resulting in a longer CDR3 and facilitating greater accessibility to the tyrosyl protein sulfotransferases. The origins of the diversity chains of these sulfated antibodies are less obvious, but it is likely that both 412d and E51 each arose from recombinations including the diversity gene 4-17, which contains the DYXDY pattern found at the CDR3 of both these antibodies.

It has become increasingly apparent in recent years that tyrosine sulfation, once thought to be a relatively minor modification, plays a common and important role in binding of many ligands to their receptors. The presence of functional sulfate groups at the ligand binding domains of—among many others—PSGL-1, the C5a receptor, and many or all of the chemokine receptors implies that properties of the tyrosine sulfate group are useful in increasing the affinity of protein associations. The heavy chain CDR3 is the most diverse and commonly the most important antigen-binding region of antibodies, and the immunoglobulin diversity genes are the most direct means by which the genome can bias the sequence of the heavy chain CDR3. Sequences encoded by these genes reflect evolutionary pressure toward high-affinity associations, and in several cases are consistent with proteins shown to be tyrosine sulfated. In light of these sequences and the data presented here, it is likely that antibody sulfation contributes to the control of pathogens in addition to HIV-1.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A peptide 15-30 amino acids in length, comprising at least 15 contiguous amino acids of SEQ ID NO:4, wherein the tyrosine residues at amino acids 19-21 must be present.

2. The peptide of claim 1, wherein one or more tyrosines in said peptide are sulfated.

3. The peptide of claim 1, wherein the tyrosine at position 12 of SEQ ID NO:4 is present in said peptide.

4. The peptide of claim 3, wherein one or more tyrosines at positions 12, 19, 20 or 21 are sulfated.

5. The peptide of claim 4, wherein at least two tyrosines at positions 12, 19, 20 or 21 are sulfated.

6. The peptide of claim 4, wherein at least three tyrosines at positions 12, 19, 20 or 21 are sulfated.

7. The peptide of claim 1, wherein said peptide consists of the amino acid sequence of SEQ ID NO:4, and wherein at least one of the tyrosines at positions 19, 20 or 21 of SEQ ID NO:4 are sulfated.

8. The peptide of claim 1, wherein said peptide is part of a fusion protein in which said peptide is joined to a sequence that inhibits the interaction between HIV and the CD4 receptor.

9. The peptide of claim 8, wherein said sequence that inhibits the interaction between HIV and the CD4 receptor is either a virus-binding peptide derived from the CD4 receptor or an antibody blocking CD4/virus binding.

10. The peptide of claim 8, wherein one or more tyrosines in said peptide are sulfated.

11. The peptide of claim 8, wherein the tyrosine at position 12 of SEQ ID NO:4 is present in said peptide.

12. The peptide of claim 11, wherein one or more tyrosines at positions 12, 19, 20 or 21 are sulfated.

13. The peptide of claim 11, wherein at least two tyrosines at positions 12, 19, 20 or 21 are sulfated.

14. The peptide of claim 11, wherein at least three tyrosines at positions 12, 19, 20 or 21 are sulfated.

15. The peptide of any one of claims 1-14, wherein said peptide reduces the uptake of an R5 HIV isolate by cultured CCR5-positive immune cells by at least 50% at a concentration of